United States Patent
Takahashi et al.

(10) Patent No.: US 8,251,913 B2
(45) Date of Patent: Aug. 28, 2012

(54) BLOOD PRESSURE MEASURING APPARATUS

(75) Inventors: Akihisa Takahashi, Kyoto (JP); Yukiya Sawanoi, Nara (JP); Osamu Shirasaki, Amagasaki (JP); Kazuomi Kario, Shimotsuke (JP)

(73) Assignee: Omron Healthcare Co., Ltd., Kyoto-shi (JP)

( * ) Notice: Subject to any disclaimer, the term of this patent is extended or adjusted under 35 U.S.C. 154(b) by 760 days.

(21) Appl. No.: 12/280,967

(22) PCT Filed: Feb. 15, 2007

(86) PCT No.: PCT/JP2007/052714
§ 371 (c)(1),
(2), (4) Date: Aug. 27, 2008

(87) PCT Pub. No.: WO2007/099775
PCT Pub. Date: Sep. 7, 2007

(65) Prior Publication Data
US 2009/0234199 A1     Sep. 17, 2009

(30) Foreign Application Priority Data

Mar. 1, 2006  (JP) ................... 2006-054916

(51) Int. Cl.
*A61B 5/02*  (2006.01)
(52) U.S. Cl. .................... 600/485; 600/481
(58) Field of Classification Search .......... 600/300–301, 600/481–499
See application file for complete search history.

(56) References Cited

U.S. PATENT DOCUMENTS

| | | |
|---|---|---|
| 2004/0049132 A1 | 3/2004 | Barron et al. |
| 2004/0230398 A1 | 11/2004 | Okada et al. |
| 2005/0054940 A1* | 3/2005 | Almen ................ 600/509 |
| 2005/0187480 A1* | 8/2005 | Kario et al. .......... 600/483 |
| 2006/0293608 A1 | 12/2006 | Rothman et al. |

FOREIGN PATENT DOCUMENTS

| | | |
|---|---|---|
| CN | 1550210 | 12/2004 |
| CN | 1660008 | 8/2005 |
| JP | 63-284611 | 11/1988 |
| JP | 8-131408 | 5/1996 |
| JP | 2000-215 A | 1/2000 |
| JP | 2001-70260 A | 3/2001 |
| JP | 2005-237472 A | 9/2005 |
| JP | 2006-102260 A | 4/2006 |
| WO | WO-01/64101 | 9/2001 |
| WO | WO-2005/018737 | 3/2005 |
| WO | WO 2005/084538 | * 9/2005 |

OTHER PUBLICATIONS

European Search Report issued Dec. 1, 2010, directed to EP 07 714 244; 7 pages. Russian Office Action dated Nov. 2, 2009, directed to counterpart Russian Application No. 2008138861; 5 pages.
International Search Report, mailed Mar. 13, 2007, directed to counterpart International Patent Application No. PCT/JP2007/052714. 4 pages.
Chinese Office Action issued on May 12, 2010 directed to counterpart application No. 200780007164.5; 4 pages.

* cited by examiner

*Primary Examiner* — Patricia Mallari
*Assistant Examiner* — Tiffany Weston
(74) *Attorney, Agent, or Firm* — Morrison & Foerster LLP

(57) ABSTRACT

A control unit determines the level of sleep of a subject on the basis of biological information measured by a biological information measuring unit starts blood pressure measurement of the subject upon determining that the determined level of sleep satisfies a predetermined condition. The control unit stores the result of the blood pressure measurement in a memory.

6 Claims, 17 Drawing Sheets

BLOOD PRESSURE MEASURING APPARATUS

REFERENCE TO RELATED APPLICATIONS

This application is a national stage application under 35 USC 371 of International Application No. PCT/JP2007/052714, filed Feb. 15, 2007, which claims the priority of Japanese Patent Application No. 2006-054916, filed Mar. 1, 2006, the contents of both of which prior applications are incorporated herein by reference.

FIELD OF THE INVENTION

The present invention relates to a blood-pressure measuring apparatus, and particularly to a blood-pressure measuring apparatus for measuring a blood pressure during sleep.

BACKGROUND OF THE INVENTION

Conventionally, it is believed that a blood pressure value is one of the most important indexes on health management, and the management of the blood pressure value is treated as important. Furthermore, recent researches show that a blood pressure measured during nighttime becomes an important index for management of a cardiovascular risk.

From such standpoints, various techniques of measuring the nighttime blood pressure have been disclosed. For example, Patent Document 1 (Japanese Unexamined Patent Publication No. 2001-70260) discloses a technique in which, in an electronic blood-pressure meter, a clock time at which the blood pressure is measured is previously set, and the blood pressure is measured at the set clock time.

In addition, Patent Document 2 (Japanese Unexamined Patent Publication No. 8-131408) discloses a technique of measuring the blood pressure as a trigger that the subject becomes in a sleep state. Specifically, in a sleep health management system disclosed in Patent Document 2, a determination whether or not body motion exists is made based on a signal obtained from a vibration sensor attached to bedclothes, the determination that the subject is in the sleep state is made when the body motion is not recognized for a predetermined time, and the blood pressure is measured as the trigger of the determination that the subject is in the sleep state.

SUMMARY OF THE INVENTION

However, in the technique disclosed in Patent Document 1, it is necessary to change the clock time set in accordance with the sleep clock time of the subject, and therefore unfortunately the operation becomes troublesome.

Even in the same subject, as shown in FIG. 18, the measured blood pressure value varies largely depending on the physical state and/or mental state during the measurement. Similarly it is thought that the fluctuation is generated depending on a sleep state (sleep depth) of the subject during the blood pressure measurement. FIG. 18 generally shows daily fluctuations in systolic blood pressure value and diastolic blood pressure value of a human. The region hatched in FIG. 18 means a period of sleep time.

Therefore, the measurement of the blood pressure value based on the sleep state of the subject is thought to be important.

In the technique disclosed in Patent Document 2, when the body motion of the subject is not observed for the predetermined time, it is recognized that the subject is in the sleep state, and the blood pressure is measured. Therefore, although it is not necessary for the subject to change the measurement clock time set in accordance with the sleep clock time, unfortunately the sleep state of the subject is not kept constant during the measurement. That is, in the technique disclosed in Patent Document 2, it is thought that the blood pressure value is measured irrespective of the sleep depth of the subject as long as the subject is asleep.

The present invention has been devised in view of the above circumstances, and it is an object of the present invention to provide a blood-pressure measuring apparatus which measures the blood pressure value on the basis of the sleep depth of the subject.

In accordance with an aspect of the present invention, a blood-pressure measuring apparatus includes a blood-pressure measuring unit which measures a blood pressure value of a subject; a level determination unit which determines one level as a level of sleep of the subject from at least three levels except for awakening; a storage unit in which information for specifying a condition for the determined level of sleep is stored; a judgment unit which judges whether or not the determined level of sleep satisfies the condition specified by the information stored in the storage unit; a blood-pressure measuring start unit which causes the blood-pressure measuring unit to start blood pressure measurement when the judgment unit judges that the determined level of sleep satisfies the condition; and a blood pressure value storage unit in which the blood pressure value of the subject measured by the blood-pressure measuring unit is stored in response to an instruction of the blood-pressure measuring start unit.

In the blood-pressure measuring apparatus according to the aspect of the present invention, preferably the blood-pressure measuring apparatus is connected to a biological information measuring unit which measures biological information on the subject, and the level determination unit determines the level of sleep of the subject based on the measurement result of the biological information measuring unit.

In the blood-pressure measuring apparatus according to the aspect of the present invention, preferably the biological information measuring unit measures a pulse of the subject, and the level determination unit determines the level of sleep of the subject based on a change in pulse wave period measured by the biological information measuring unit.

In the blood-pressure measuring apparatus according to the aspect of the present invention, preferably the biological information measuring unit measures a body temperature of the subject, and the level determination unit determines the level of sleep of the subject based on a change in body temperature measured by the biological information measuring unit.

In the blood-pressure measuring apparatus according to the aspect of the present invention, preferably the judgment unit judges that the condition is satisfied when a depth of the determined level of sleep reaches the deepest level in levels which can be determined by the level determination unit.

In the blood-pressure measuring apparatus according to the aspect of the present invention, preferably the judgment unit judges that the condition is satisfied when a depth of the determined level of sleep is changed from the second shallowest level to the shallowest level in levels which can be determined by the level determination unit.

In the blood-pressure measuring apparatus according to the aspect of the present invention, preferably the level determination unit determines the level of sleep at constant time intervals, and the judgment unit judges that the condition is satisfied when the level of sleep determined by the level determination unit is changed larger than a specific change amount with respect to the level of sleep previously determined by the level determination unit.

According to the present invention, one level is determined as the level of sleep of the subject from at least three levels except for awakening, and the blood pressure value is stored when the determined level of sleep satisfies the predetermined condition.

Therefore, the blood pressure value is stored as the measurement value when the sleep depth of the subject satisfies the predetermined condition.

Therefore, the blood pressure value can be measured based on the sleep depth of the subject during non-REM (non-Rapid Eye Movement) sleep, uprising or the like suitable to the measurement of the blood pressure value. Because the subject is mentally settled during the non-REM sleep, it is expected that the health condition of the subject appears prominently. As shown in FIG. 18, because generally the blood pressure value of the subject is rapidly increased during the uprising, it is thought that the uprising is suitable to measurement of the blood pressure value in order to estimate a health management risk.

DETAILED DESCRIPTION OF THE INVENTION

A blood-pressure measuring apparatus according to an exemplary embodiment of the present invention will be described below with reference to the drawings.

[First Embodiment]

Figure 1:
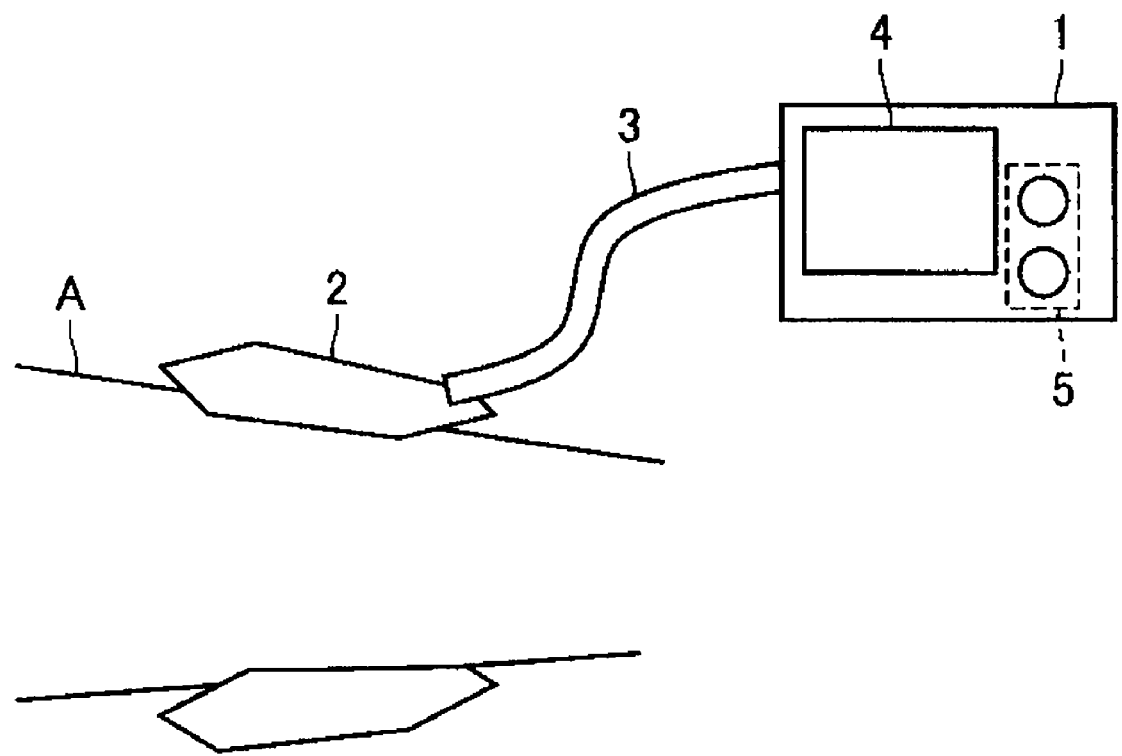
FIG. 1 is a schematic view showing a blood-pressure measuring apparatus according to a first embodiment of the present invention.

FIG. 1 is a schematic view showing a blood-pressure measuring apparatus according to a first embodiment of the present invention.

A blood-pressure measuring apparatus 1 includes a cuff 2, and the blood pressure of the subject is measured while the cuff 2 is wound around an arm A of the subject.

The blood-pressure measuring apparatus 1 includes a display device 4 and an operation unit 5 in a front surface thereof. The operation unit 5 includes a plurality of operation buttons. The blood-pressure measuring apparatus 1 includes a tube 3 which connects a built-in pump (pump 32 described later) and the cuff 2. The cuff 2 accommodates an inflatable bladder therein as described later.

Figure 2:
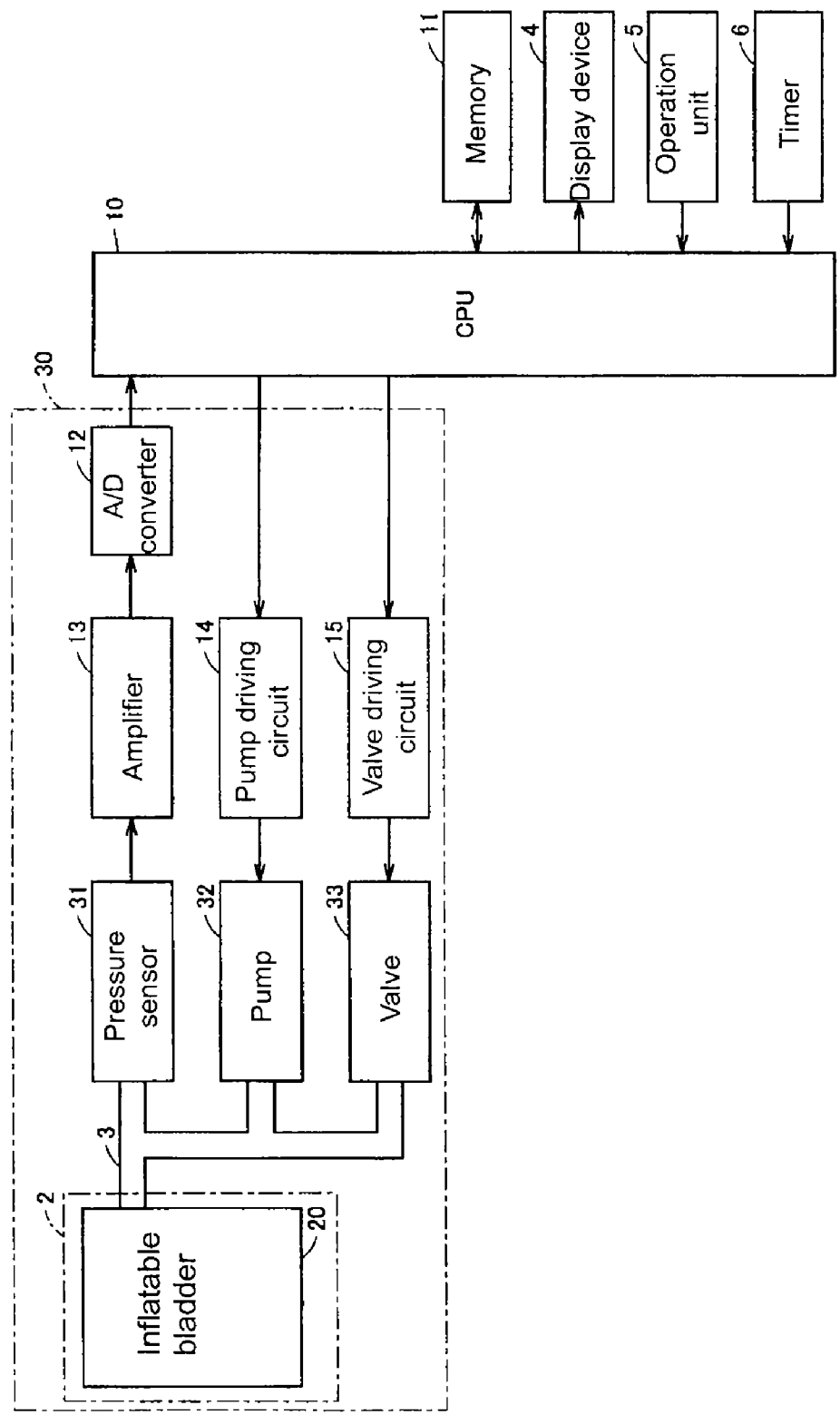
FIG. 2 is a schematic diagram showing a hardware configuration of the blood-pressure measuring apparatus of FIG. 1.

FIG. 2 is a schematic diagram showing a hardware configuration of the blood-pressure measuring apparatus 1. In addition to the display device 4 and the operation unit 5, the blood-pressure measuring apparatus 1 includes CPU (Central Processing Unit) 10 which wholly controls an operation of the blood-pressure measuring apparatus 1, a memory 11 in which various pieces of information are stored, a timer 6, and a biological information measuring unit 30.

In addition to the cuff 2 and the tube 3, the biological information measuring unit 30 includes a pressure sensor 31 which measures a pressure of an inflatable bladder 20, an amplifier 13 which is connected to the pressure sensor 31, an A/D (Analog/Digital) conversion unit 12 which converts analog data supplied from the pressure sensor 31 through the amplifier 13 into digital data and supplies the digital data to CPU 10, a pump 32 which supplies air into the inflatable bladder 20, a pump driving circuit 14 which drives the pump 32, a valve 33 which opens and closes a connection portion between the tube 3 and the pump 32, and a valve driving circuit 15 which drives the valve 33.

In the blood-pressure measuring apparatus 1, data supplied from the pressure sensor 31 is fed into CPU 10 through the A/D converter 12, CPU 10 controls the operation of the pump 32 through the pump driving circuit 14, and CPU 10 controls the opening and closing of the valve 33 through the valve driving circuit 15.

In addition to the measurement of the blood pressure value of the subject, the blood-pressure measuring apparatus 1 can measure the pulse of the subject on the basis of the data supplied from the pressure sensor 31 by filling the inflatable bladder 20 with air having a pressure as low as about 20 to about 30 mmHg.

Figure 3:
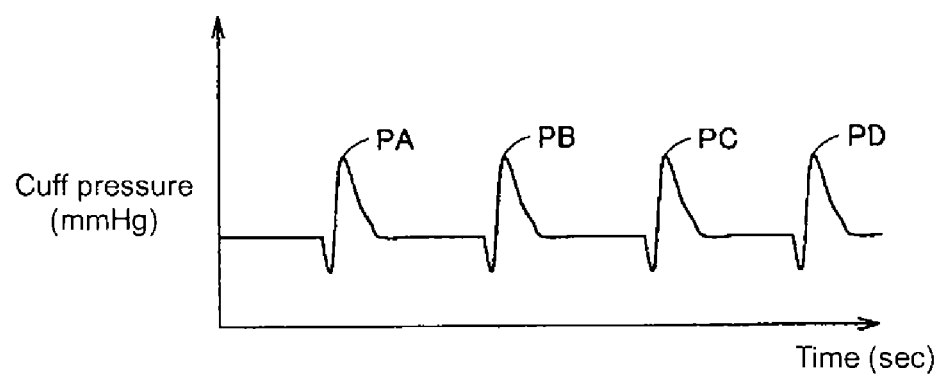
FIG. 3 shows an example of a temporal change in pulse measured based on data supplied from a pressure sensor of the blood-pressure measuring apparatus of FIG. 1.

FIG. 3 shows an example of the pulse which is measured based on the data supplied from the pressure sensor 31. The data shown in FIG. 3 corresponds to data which is supplied from the A/D converter 12 while the inflatable bladder 20 is filled with the air having a proper pressure as described above.

Referring to FIG. 3, peaks PA to PD of the pulse are shown. In the blood-pressure measuring apparatus 1, CPU 10 detects the plurality of peaks by continuously measuring the pulses to some extent, and CPU 10 obtains a pulse wave period of a predetermined period (time during which the pulses are continuously measured to some extent) by computing an average value of time intervals between peaks adjacent to each other. It is thought that the number of peaks used to compute the average value is appropriately set.

In the blood-pressure measuring apparatus 1, the pulse of the subject is measured during sleep, the pulse wave period is computed based on the pulse measurement result, and the blood pressure value of the subject is measured when the change in pulse wave period (for example, a ratio of the computed pulse wave period to the pulse wave period immediately after the sleep) satisfies a predetermined condition.

Figure 4:
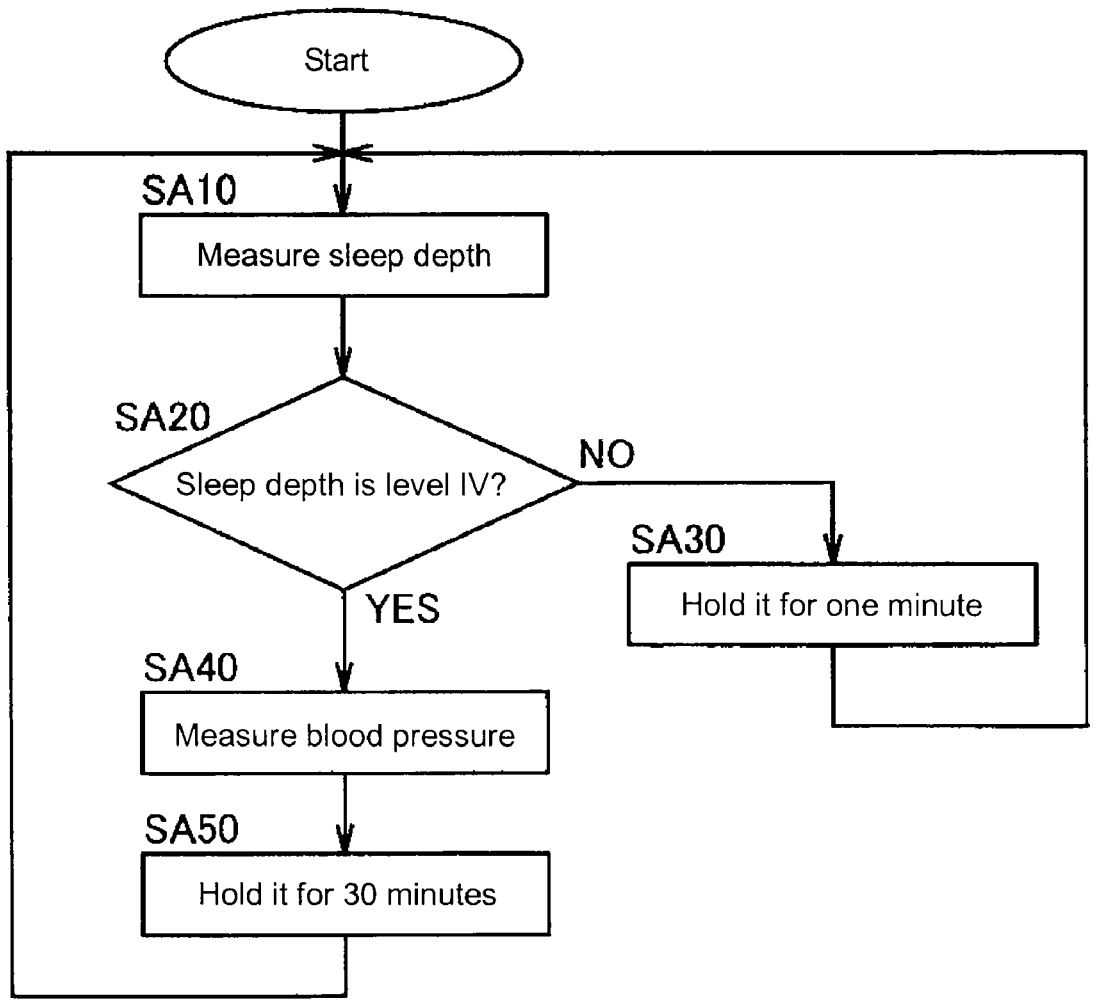
FIG. 4 is a flowchart showing a process for measuring a blood pressure value of a subject in the blood-pressure measuring apparatus of FIG. 1.

Specifically, in the blood-pressure measuring apparatus 1, the pulse wave period immediately after the sleep of the subject is computed, and the blood pressure value of the subject is measured during the sleep of the subject. Therefore, the process shown in FIG. 4 is performed. The pulse wave period immediately after the sleep shall mean a pulse wave period computed as follows: A switch is provided in the blood-pressure measuring apparatus 1, the switch is turned on when the subject starts the sleep, and the pulse wave period is computed after a predetermined time (for example, 5 to 10 minutes) elapses since the switch is turned on. The computed pulse wave period immediately after the sleep is stored in the memory 11.

Referring to FIG. 4, in step SA10, CPU 10 measures a sleep depth (level of sleep) of the subject, and the process proceeds to step SA20. The sleep depth measurement in step SA10 includes the following processes.

(1) The pulse of the subject is measured in a predetermined period.

(2) The pulse wave period is computed based on the pulse measurement result of the subject in the predetermined period.

(3) The sleep depth is determined by utilizing the change in pulse wave period computed.

A correspondence relationship between the pulse wave period and the sleep depth shown in Table 1 is referred to when the sleep depth is determined based on the change in pulse wave period. In Table 1, the letter CA designates a pulse wave period immediately after sleep stored in the memory 11, and the letter CP designates a pulse wave period computed at that time. For example, the correspondence relationship shown in Table 1 is previously stored in the memory 11.

TABLE 1

| Sleep depth | Condition for pulse wave period CP |
| --- | --- |
| REM | $CP \leq CA \times 1.05$ |
| Non-REM I | $CA \times 1.05 < CP \leq CA \times 1.10$ |
| Non-REM II | $CA \times 1.10 < CP \leq CA \times 1.15$ |
| Non-REM III | $CA \times 1.15 < CP \leq CA \times 1.20$ |
| Non-REM IV | $CA \times 1.20 < CP \leq CA \times 1.25$ |

As can be seen from Table 1, in the first embodiment, the sleep depth is defined by five stages according to the CP value. The five stages include REM (Rapid Eye Movement), non-REM I, non-REM II, non-REM III, and non-REM IV. In the description, non-REM I is deeper than REM in the sleep depth, non-REM II is deeper than non-REM I in the sleep depth, non-REM III is deeper than non-REM II in the sleep depth, and non-REM IV is deeper than non-REM III in the sleep depth.

In step SA20, CPU 10 determines whether or not the sleep depth measured (determined) in step SA10 is the sleep depth IV. The process proceeds to step SA40 when the determination is affirmative, and the process proceeds to step SA30 when the determination is not affirmative.

In step SA30, CPU 10 holds it for one minute, and the process returns to step SA10.

In step SA40, because the sleep depth is the sleep depth IV, CPU 10 makes a transition to a routine for starting the blood pressure measurement, CPU 10 starts the blood pressure measurement of the subject, and CPU 10 stores the measurement result in the memory 11. Then, the process proceeds to step SA50. In the blood-pressure measuring apparatus 1, when the blood pressure value is measured, the inflatable bladder 20 is filled with air having a pressure higher than that of the pulse measurement, and the pressure change is detected by the pressure sensor 31. In step SA40, preferably the sleep depth during the measurement and the measurement clock time are also stored in the memory 11 while correlated with the measurement result.

In step SA50, CPU 10 holds it for 30 minutes, and the process returns to step SA10. CPU 10 holds it for 30 minutes in step SA50, which allows the measurement of the blood pressure to be avoided until the next peak of the sleep depth comes since the blood pressure is measured at the peak (deepest sleep depth) of the sleep depth. That is, the plurality of blood pressure measurements can be avoided at the peak of the same sleep depth.

In the first embodiment, the sleep depth is determined based on the change in pulse wave period of the subject, the blood pressure measurement of the subject is started when the sleep depth becomes the deepest (deepest sleep, that is, deepest peak), and the measured blood pressure is recorded. Therefore, the blood pressure value can be measured when the subject is thought to be most settled mentally.

It is assumed that the condition at which sleep depth the blood pressure measurement is started is stored in the memory 11. That is, in the first embodiment, information of "sleep depth IV" is stored in a predetermined area of the memory 11. In step SA20, actually CPU 10 determines whether or not the sleep depth at that time satisfies the condition stored in the area of the memory 11. The process proceeds to step SA40 when the sleep depth satisfies the condition, and the process proceeds to step SA30 when the sleep depth does not satisfy the condition.

Figure 5:
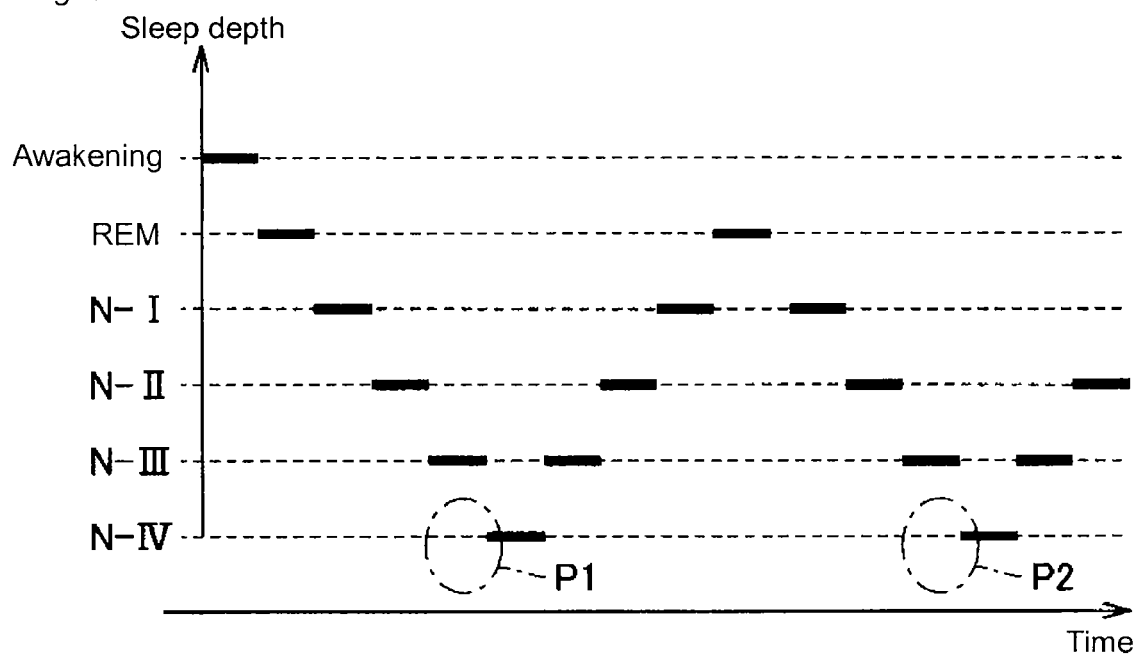
FIG. 5 is a diagram for explaining a time the blood pressure value is measured and stored in the process of FIG. 4.

FIG. 5 shows a general mode of the change in sleep depth. FIG. 5 is a diagram for explaining the time the blood pressure value is measured and stored in step SA40 of the process shown in FIG. 4. In FIG. 5, a vertical axis indicates the sleep depth (non-REM is abbreviated to "N"), and a horizontal axis indicates a time elapsed from the sleep start. In FIG. 5, the measured sleep depth is shown by a thick line.

The sleep depth is changed so as to return to REM after becoming deeper from REM to non-REM IV, and the change is observed on a substantially periodic basis. Generally the period of the sleep depth ranges from 60 minutes to 90 minutes.

In the process of FIG. 4, the blood pressure measurement is started under the condition that the sleep depth becomes non-REM IV, and the blood pressure value is recorded. It is said that the blood pressure value is measured at the time the measurement values (thick lines) of the sleep depth shown in FIG. 5 enter circles P1 and P2.

In the process of FIG. 4, because the blood pressure value is measured when the sleep depth becomes the maximum value (maximum value in depth, that is, the locally deepest peak of the sleep), the blood pressure value is measured under the condition that the sleep depth becomes non-REM IV. That is, it is assumed that the time the sleep depth reaches non-REM IV is the time the sleep depth becomes the deepest peak, and the blood pressure value is measured.

[Second Embodiment]

A blood-pressure measuring apparatus 1 according to a second embodiment of the present invention has a hardware configuration similar to that of the blood-pressure measuring apparatus 1 of the first embodiment.

The blood-pressure measuring apparatus 1 of the second embodiment differs from the blood-pressure measuring apparatus 1 of the first embodiment in contents of the process performed to measure the blood pressure of the subject. The process performed to measure the blood pressure value by the blood-pressure measuring apparatus 1 of the second embodiment will be described below with reference to a flowchart of FIG. 6.

In step SB10, similarly to step SA10, CPU 10 measures the sleep depth of the subject, and the process proceeds to step SB20.

In step SB20, CPU 10 determines whether or not a rate of change ($\alpha$) of the sleep depth measured (determined) in the last step SB10 to the sleep depth measured (determined) in the second last step SB10 has a positive value. The rate of change $\alpha$ becomes the positive value when the sleep depth measured in the last step SB10 is shifted shallower than the sleep depth measured in the second last step SB10. The process proceeds to step SB40 when the rate of change a is positive, and the process proceeds to step SB30 when the rate of change $\alpha$ is not positive.

In step SB30, CPU 10 holds it for one minute, and the process returns to step SB10.

In step SB40, CPU 10 measures the blood pressure value of the subject, the measurement result is stored in the memory 11, and the process proceeds to step SB50. At this point, preferably the sleep depth during the measurement and the measurement clock time are also stored while correlated with the measurement result.

In step SB50, CPU 10 holds it for 30 minutes, and the process returns to step SB10.

In the second embodiment, the sleep depth is determined based on the change in pulse wave period of the subject, and the blood pressure of the subject is measured when the determined sleep depth is changed shallower than the previously-determined sleep depth.

It is assumed that the condition at which sleep depth the blood pressure measurement is started is stored in the memory 11. That is, in the second embodiment, for example, a value of "0" is stored in a predetermined area of the memory 11. In step SB20, actually CPU 10 compares the rate of change ($\alpha$) at that time to a value stored in the area. The process proceeds to step SB40 when the rate of change ($\alpha$) at that time is more than the value stored in the area, and the process proceeds to step SB30 when the rate of change ($\alpha$) at that time is not more than the value stored in the area.

Figure 6:
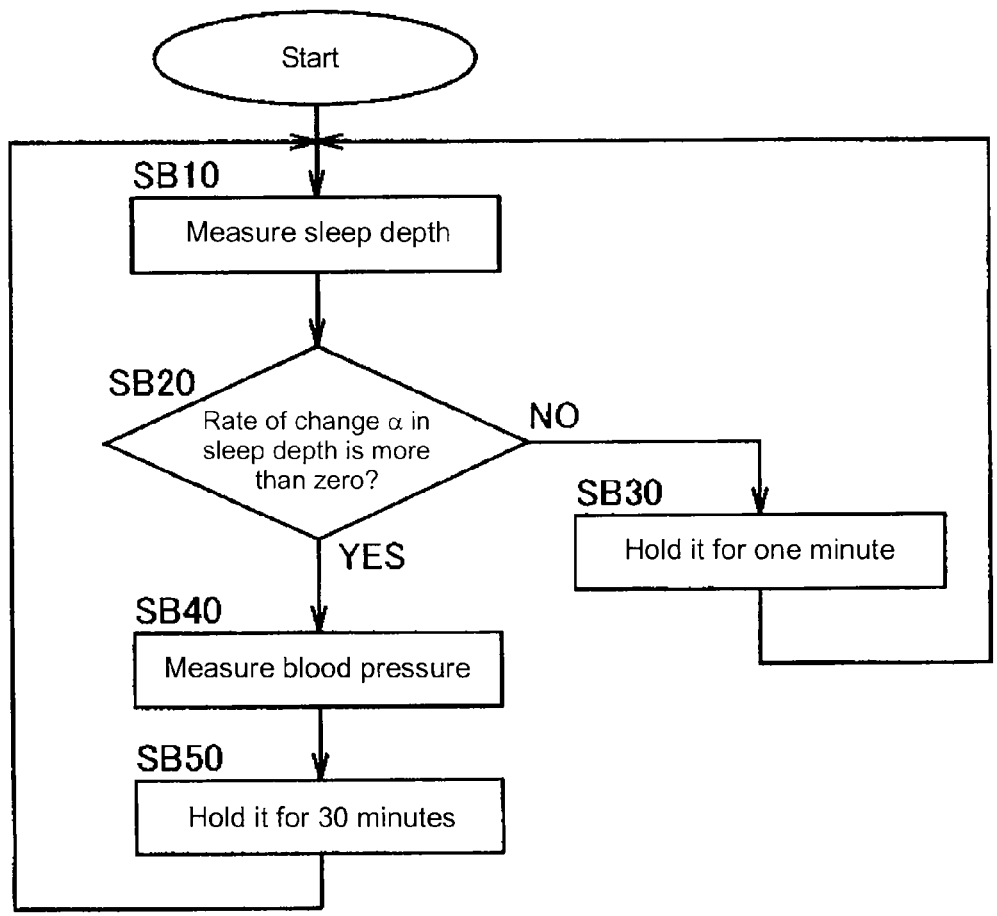
FIG. 6 is a flowchart showing a process performed to measure the blood pressure value of the subject in a blood-pressure measuring apparatus according to a second embodiment of the present invention.
Figure 7:
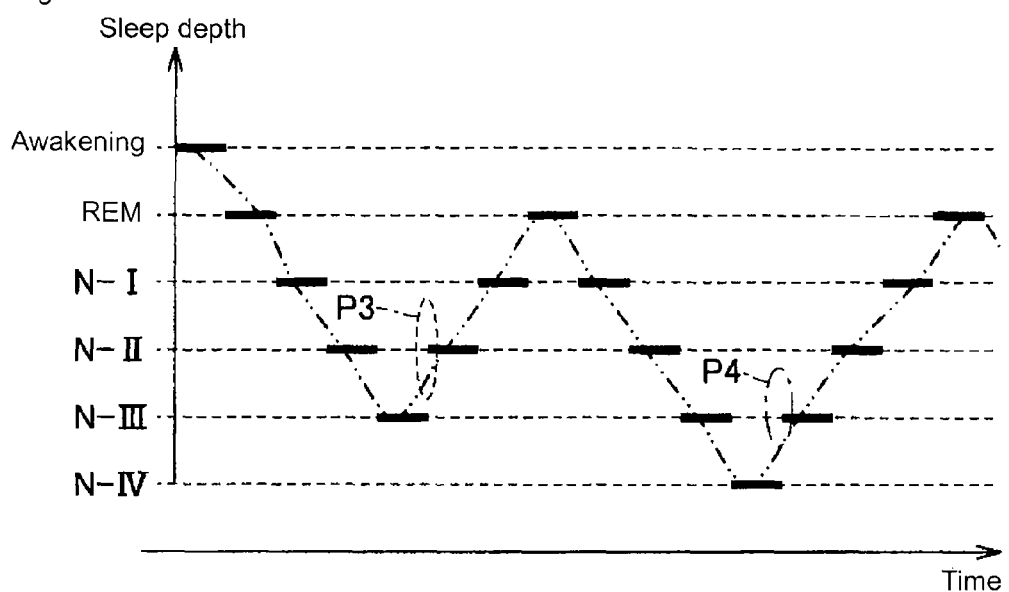
FIG. 7 is a diagram for explaining a time the blood pressure value is measured and stored in the process of FIG. 6.

FIG. 7 is a diagram for explaining the time the blood pressure value is measured and stored in step SB40 of the process of FIG. 6. In FIG. 7, similarly to FIG. 5, the vertical axis indicates the sleep depth, and the horizontal axis indicates the time elapsed from the sleep start. In FIG. 7, the measured sleep depth is shown by the thick line.

The sleep depth is changed so as to return to REM after becoming deeper from REM to non-REM IV, and the change is observed on the substantially periodic basis. Generally the period of the sleep depth ranges from 60 minutes to 90 minutes.

In the process of FIG. 6, it is said that the blood pressure value is measured when the determined sleep depth is changed shallower than the previously-determined sleep depth, that is, at the time the measurement values (thick lines) of the sleep depth shown in FIG. 7 enter circles P3 and P4.

In the process of FIG. 6, because the blood pressure value is measured when the sleep depth becomes the maximum value (maximum value in depth, that is, the locally deepest peak of the sleep), the blood pressure value is measured under the condition that the determined sleep depth is changed shallower than the previously-determined sleep depth. That is, it is assumed that the time the sleep depth is changed to shallower than the previously-determined sleep depth is the time the sleep depth becomes the maximum value, the measurement of the blood pressure value is started, and the measured blood pressure value is recorded.

[Third Embodiment]

A blood-pressure measuring apparatus 1 according to a third embodiment of the present invention has a hardware configuration similar to that of the blood-pressure measuring apparatus 1 of the first embodiment.

The blood-pressure measuring apparatus 1 of the third embodiment differs from the blood-pressure measuring apparatus 1 of the first embodiment in contents of the process performed to measure the blood pressure of the subject. The process performed to measure the blood pressure value by the blood-pressure measuring apparatus 1 of the third embodiment will be described below with reference to a flowchart of FIG. 8.

In step SC10, similarly to step SA10, CPU 10 measures the sleep depth of the subject, and the process proceeds to step SC20.

In step SC20, CPU 10 determines whether or not the sleep depth measured (determined) in the second last step SC10 is non-REM I while the sleep depth measured (determined) in the last step SC10 is REM. The process proceeds to step SC40 when the determination is affirmative, and the process proceeds to step SC30 when the determination is not affirmative.

In step SC30, CPU 10 holds it for one minute, and the process returns to step SC10.

In step SC40, CPU 10 measures the blood pressure value of the subject, the measurement result is stored in the memory 11, and the process proceeds to step SC50. At this point, preferably the sleep depth during the measurement and the measurement clock time are also stored while correlated with the measurement result.

In step SC50, CPU 10 holds it for 30 minutes, and the process returns to step SC10.

In the third embodiment, the sleep depth is determined based on the change in pulse wave period of the subject, and the blood pressure of the subject is measured when the determined sleep depth is REM which is changed from non-REM I.

It is assumed that the condition at which sleep depth the blood pressure measurement is started is stored in the memory 11. That is, in the third embodiment, for example, information indicating a pattern of the change in sleep depth, specifically information indicating a pattern of the sleep depth changed from non-REM I to REM is stored in a predetermined area of the memory 11. In step SC20, actually CPU 10 compares the pattern of the change in sleep depth at that time (patterns of the sleep depth determined in the last step SC10 and the sleep depth determined in the second last step SC10) to the pattern stored in the area. The process proceeds to step SC40 when the patterns are matched with each other, and the process proceeds to step SC30 when the patterns differ from each other.

Figure 8:
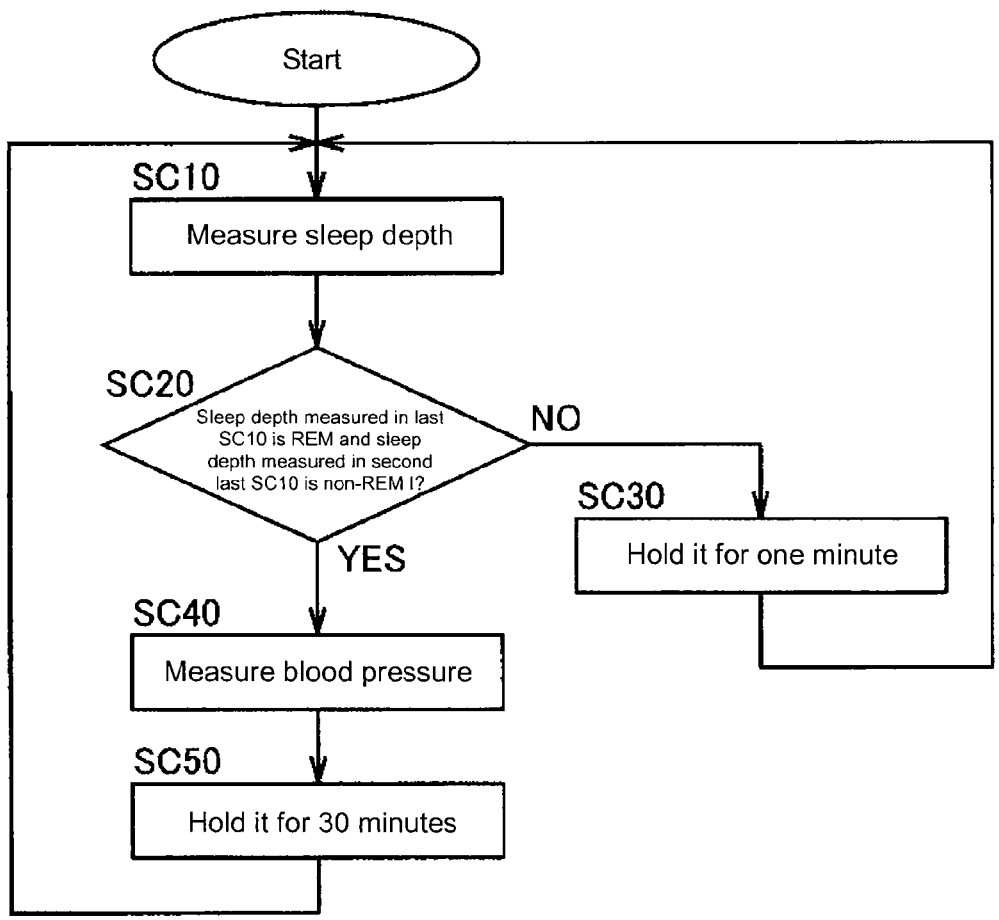
FIG. 8 is a flowchart showing a process performed to measure the blood pressure value of the subject in a blood-pressure measuring apparatus according to a third embodiment of the present invention.
Figure 9:
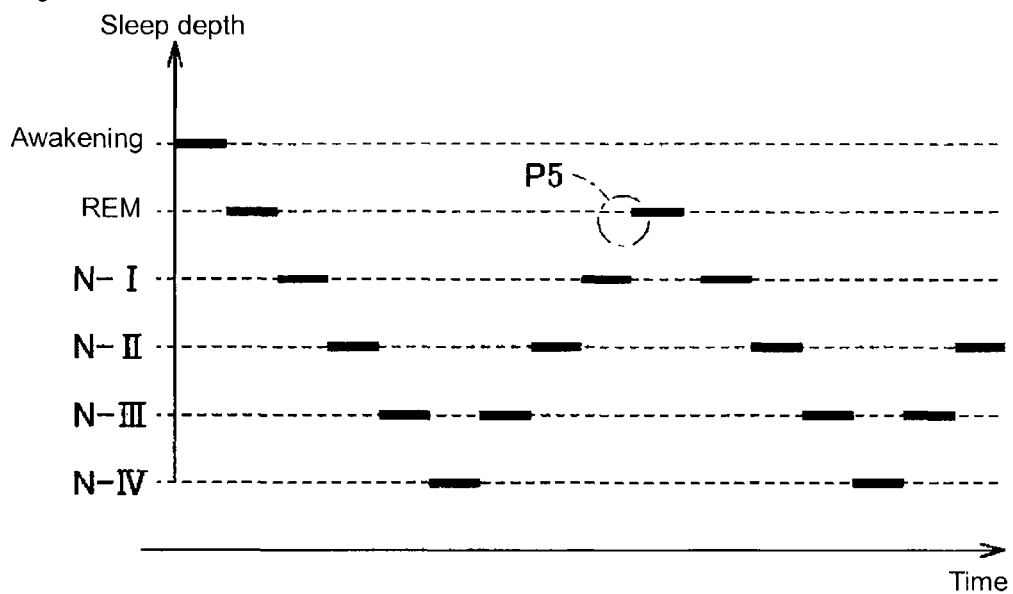
FIG. 9 is a diagram for explaining a time the blood pressure value is measured and stored in the process of FIG. 8.

FIG. 9 is a diagram for explaining the time the blood pressure value is measured and stored in step SC40 of the process of FIG. 8. In FIG. 9, similarly to FIG. 5, the vertical axis indicates the sleep depth, and the horizontal axis indicates the time elapsed from the sleep start. In FIG. 9, the measured sleep depth is shown by the thick line. In FIG. 9, the sleep depth is changed so as to return to REM after becoming deeper from REM to non-REM IV, and the change is observed on the substantially periodic basis. Generally the period of the sleep depth ranges from 60 minutes to 90 minutes.

In the process of FIG. 8, it is said that the blood pressure value is measured when the currently-determined sleep depth is REM while the previously-determined sleep depth is non-REM I, that is, at the time the measurement values (thick lines) of the sleep depth shown in FIG. 9 enter a circle P5.

In the process of FIG. 8, because the blood pressure value is measured when the sleep depth becomes the minimum value (minimum value in depth, that is, the locally shallowest peak of the sleep), the blood pressure value measurement is started under the condition that the sleep depth is changed from non-REM I to REM, and the measured blood pressure value is recorded. That is, it is assumed that the time the sleep depth is changed from non-REM I to REM is the time the sleep depth becomes the minimum value, and the blood pressure value is measured.

[Fourth Embodiment]

A blood-pressure measuring apparatus 1 according to a fourth embodiment of the present invention has a hardware configuration similar to that of the blood-pressure measuring apparatus 1 of the first embodiment.

The blood-pressure measuring apparatus 1 of the fourth embodiment differs from the blood-pressure measuring apparatus 1 of the first embodiment in contents of the process performed to measure the blood pressure of the subject. The process performed to measure the blood pressure value by the blood-pressure measuring apparatus 1 of the fourth embodiment will be described below with reference to a flowchart of FIG. 10.

In step SD10, similarly to step SA10, CPU 10 measures the sleep depth of the subject, and the process proceeds to step SD20.

In step SD20, CPU 10 determines whether or not the sleep depth measured (determined) in the last step SD10 is non-REM IV. The process proceeds to step SD30 when the determination is affirmative, and the process proceeds to step SD50 when the determination is not affirmative.

In step SD30, similarly to step SA40, CPU 10 measures the blood pressure value of the subject, the measurement result is stored in the memory 11, and the process proceeds to step SD40.

In step SD40, CPU 10 holds it for 30 minutes, and the process returns to step SD10.

In step SD50, CPU 10 determines whether or not the sleep depth measured in the last step SD10 is changed shallower by at least two stages from the sleep depth measured in the second last step SD10, for example, the sleep depth measured in the last step SD10 is changed from non-REM II to REM or from non-REM III to non-REM I. The process proceeds to step SD30 when the determination is affirmative, and the process proceeds to step SD60 when the determination is not affirmative.

In step SD60, CPU 10 holds it for one minute, and the process returns to step SD10.

In the fourth embodiment, the sleep depth is determined based on the change in pulse wave period of the subject, and the blood pressure of the subject is measured and the measured blood pressure value is recorded when the determined sleep depth is non-REM IV or when the determined sleep depth is rapidly changed shallower (changed shallower by at least two stages from the previously-measured sleep depth).

It is assumed that the condition at which sleep depth the blood pressure measurement is started is stored in the memory 11. That is, in the fourth embodiment, information indicating that the determined sleep depth is non-REM IV or the determined sleep depth is changed shallower by at least two stages from the previous measurement sleep depth is stored in a predetermined area of the memory 11. In steps SD20 and SD30, actually CPU 10 determines whether or not the sleep depth state at that time satisfies the condition defined by the information stored in the area. The process proceeds to step SD40 when the condition is satisfied, and the process proceeds to step SD60 when the condition is not satisfied.

Figure 10:
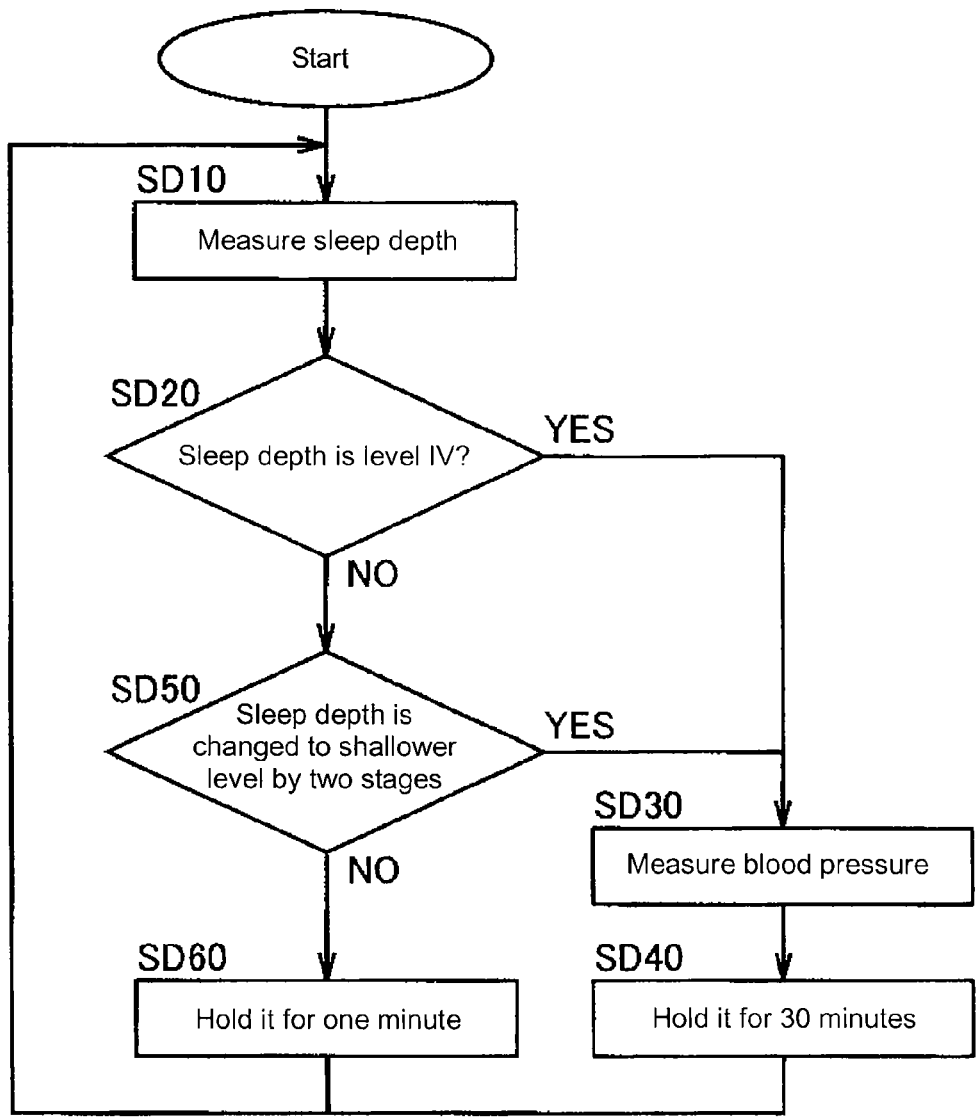
FIG. 10 is a flowchart showing a process performed to measure the blood pressure value of the subject in a blood-pressure measuring apparatus according to a fourth embodiment of the present invention.
Figure 11:
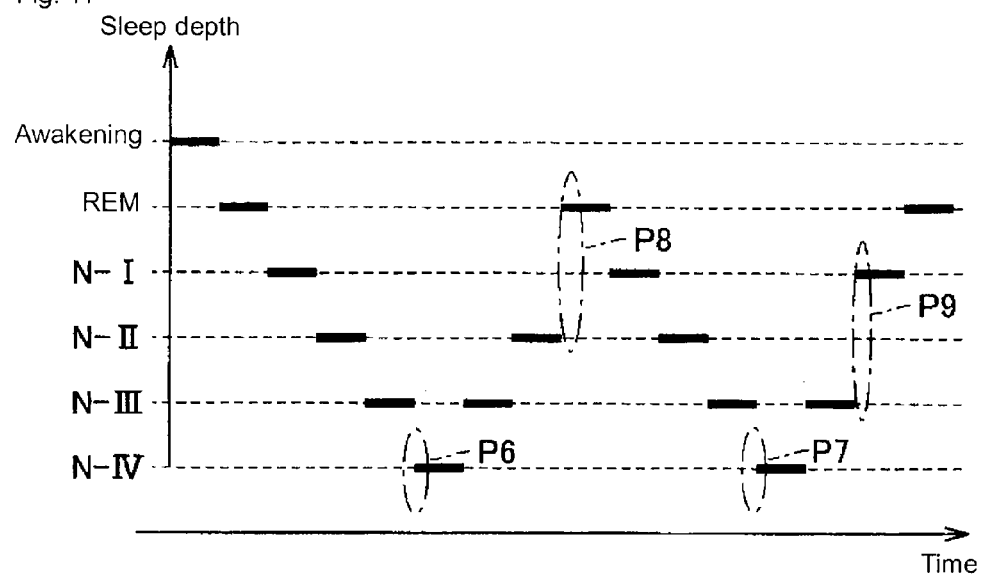
FIG. 11 is a diagram for explaining a time the blood pressure value is measured and stored in the process of FIG. 10.

FIG. 11 is a diagram for explaining the time the blood pressure value is measured and stored in step SD30 of the process of FIG. 10. In FIG. 11, similarly to FIG. 5, the vertical axis indicates the sleep depth, and the horizontal axis indicates the time elapsed from the sleep start. In FIG. 11, the measured sleep depth is shown by the thick line. In FIG. 11, the sleep depth is changed so as to return to REM after becoming deeper from REM to non-REM IV, and the change is observed on the substantially periodic basis. Generally the period of the sleep depth ranges from 60 minutes to 90 minutes.

In the process of FIG. 10, it is said that the blood pressure value is measured when the sleep depth is non-REM IV and when the currently-determined sleep depth is shifted shallower by at least two stages from the previously-determined sleep depth, that is, at the time the measurement values (thick lines) of the sleep depth shown in FIG. 11 enter circles P6 to P9.

In the process of FIG. 10, because CPU 10 holds it for 30 minutes in step SD40, the sleep depth is thought to be shifted shallower by at least two stages in 30 minutes when CPU 10 determines that the sleep depth is shifted shallower by at least two stages from the previously-determined sleep depth in step SD 50. The case where the subject is in an apneic state can be cited as a specific example of the case where the sleep depth is rapidly changed shallower.

In the process of FIG. 10, the blood pressure value may be detected when the sleep depth is shifted deeper by at least a predetermined stage.

Figure 12:
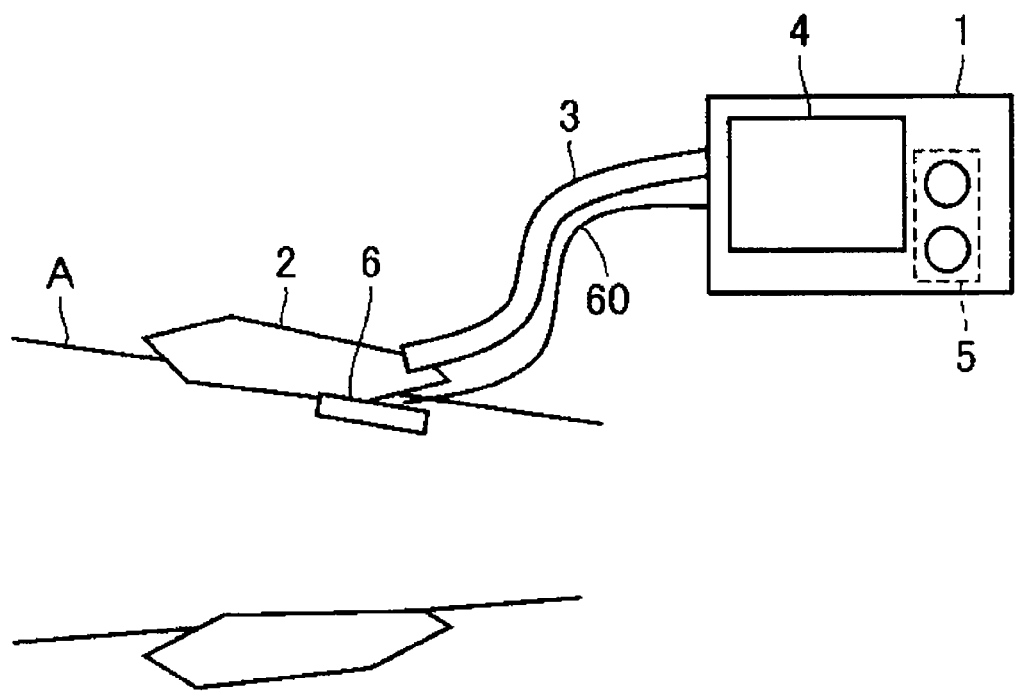
FIG. 12 is a schematic view showing a blood-pressure measuring apparatus according to a fifth embodiment of the present invention.

[Fifth Embodiment]FIG. 12 is a schematic view showing a blood-pressure measuring apparatus according to a fifth embodiment of the present invention.

The fifth embodiment differs from the first to fourth embodiments in that the biological information on the subject measured to determine the sleep depth is changed. The change of the fifth embodiment will mainly be described below.

Referring to FIG. 12, compared with the blood-pressure measuring apparatus 1 of the first to fourth embodiments, a blood-pressure measuring apparatus 1 of the fifth embodiment further includes a body temperature sensor 6 for measuring a body temperature which is of the biological information on the subject. The body temperature sensor 6 is provided in the cuff 2, and the body temperature sensor 6 is located on the side where the cuff 2 abuts on the arm A of the subject. The body temperature sensor 6 may be formed independently of the cuff 2.

Figure 13:
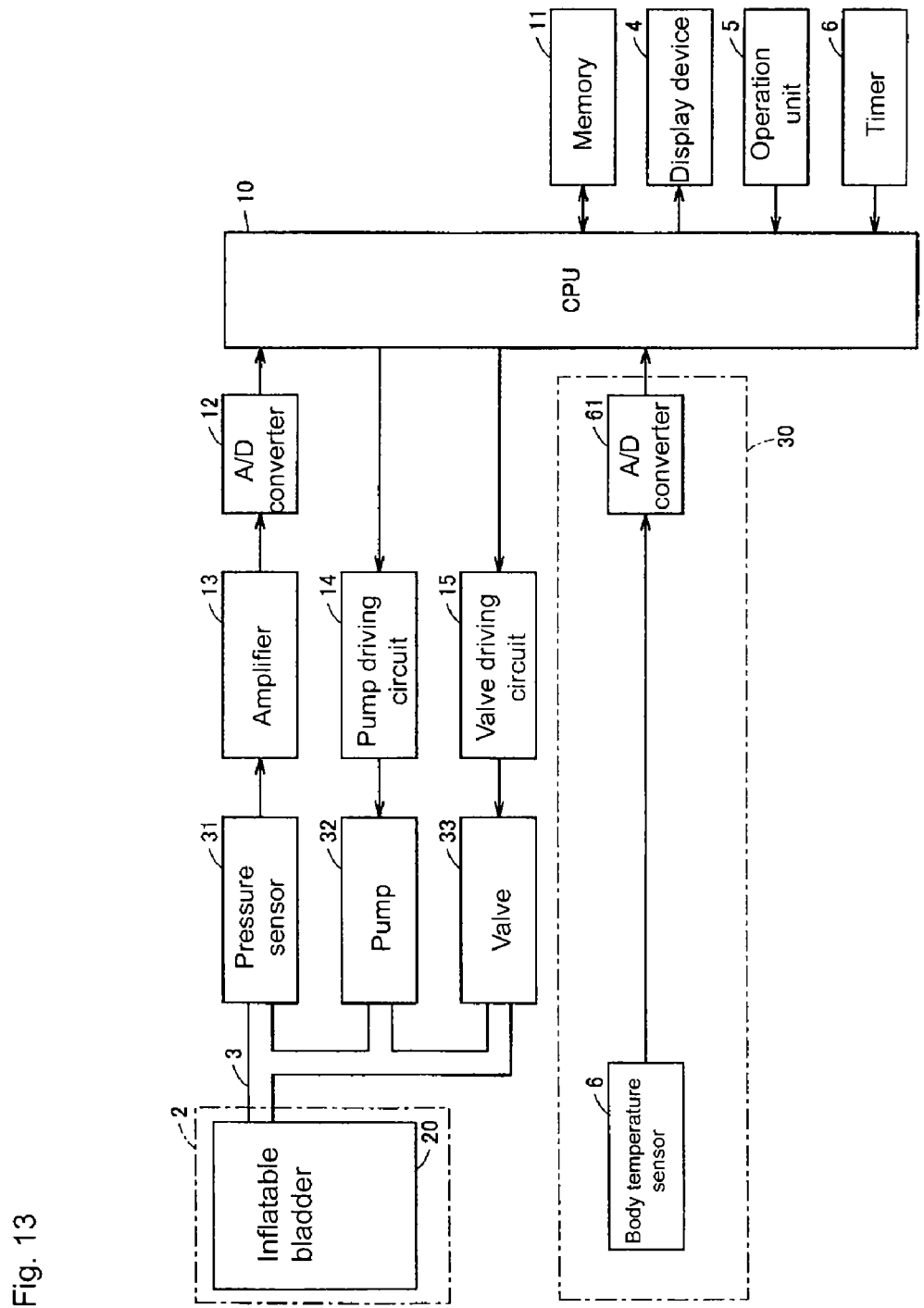
FIG. 13 is a schematic diagram showing a hardware configuration of the blood-pressure measuring apparatus of FIG. 12.

FIG. 13 is a schematic diagram showing a hardware configuration of the blood-pressure measuring apparatus 1 of FIG. 12. Compared with the blood-pressure measuring apparatus 1 of the first to fourth embodiments, the blood-pressure measuring apparatus 1 of the fifth embodiment includes the body temperature sensor 6 and an A/D converter 61. The A/D converter 61 converts the data concerning the body temperature of the subject detected by the body temperature sensor 6 into the digital data, and the A/D converter 61 transmits the digital data to CPU 10.

In the fifth embodiment, for example, as shown in Table 2, information (for example a table) in which a change in body temperature value of the subject and the sleep depth are correlated with each other is stored in the memory 11. Specifically, in the information, a range of a body temperature value T measured is defined by the five stages of REM to non-REM IV.

TABLE 2

| Sleep depth | Condition for body temperature T |
| --- | --- |
| REM | Body temperature immediately after sleep $-0.3°$ C. $\leq$ T |
| Non-REM I | Body temperature immediately after sleep $-0.6°$ C. $<$ T $\leq$ Body temperature immediately after sleep $-0.3°$ C. |
| Non-REM II | Body temperature immediately after sleep $-0.9°$ C. $<$ T $\leq$ Body temperature immediately after sleep $-0.6°$ C. |
| Non-REM III | Body temperature immediately after sleep $-1.2°$ C. $<$ T $\leq$ Body temperature immediately after sleep $-0.9°$ C. |
| Non-REM IV | Body temperature immediately after sleep $-1.5°$ C. $<$ T $\leq$ Body temperature immediately after sleep $-1.2°$ C. |

Figure 14:
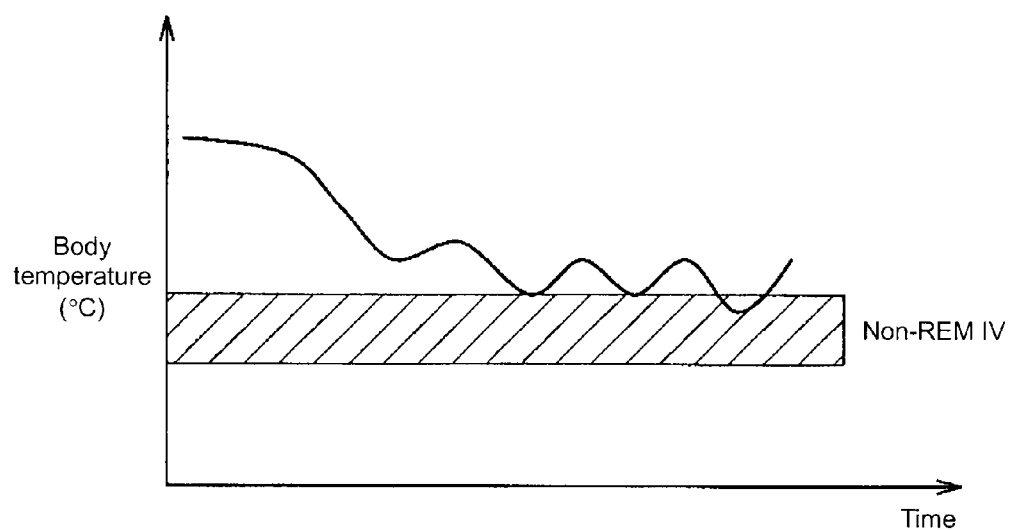
FIG. 14 is a diagram showing an example of a change in body temperature of the subject as sleeping hours advances, which is measured in the blood-pressure measuring apparatus of FIG. 12.

FIG. 14 is a diagram showing an example of the change in body temperature of the subject as sleeping hours advance, which is measured in the blood-pressure measuring apparatus 1 of the fifth embodiment.

As can be seen from FIG. 14, although the body temperature is lowered as a whole as the sleeping hours advance, the body temperature repeatedly goes up and down in a local predetermined period. A region of the body temperature at which the sleep depth is set to non-REM IV is hatched in FIG. 14.

The fifth embodiment differs from the first to fourth embodiments only in that the biological information measured to determine the sleep depth is changed. That is, the control content in which the determined sleep depth is utilized is similar to those of the first to fourth embodiments.

[Sixth Embodiment]

Figure 15:
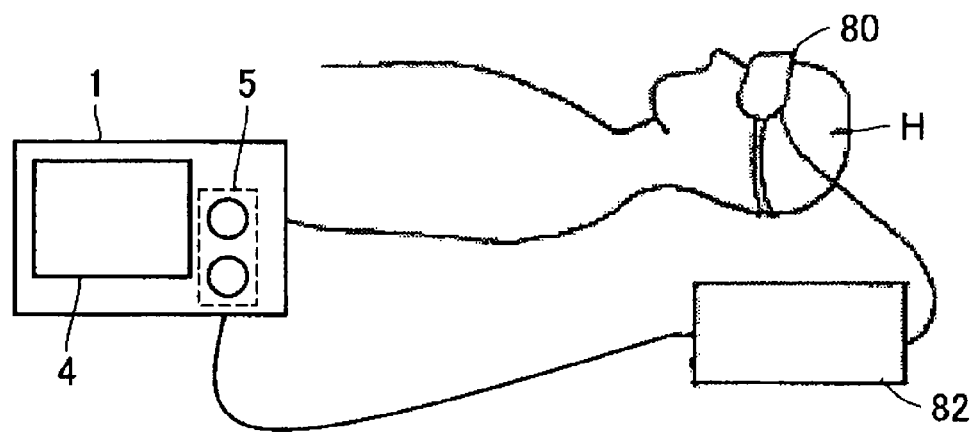
FIG. 15 is a schematic view showing a blood-pressure measuring apparatus according to a sixth embodiment of the present invention.

FIG. 15 is a schematic view showing a blood-pressure measuring apparatus according to a sixth embodiment of the present invention.

The sixth embodiment differs from the first to fourth embodiments in that the biological information on the subject measured to determine the sleep depth is changed. The change of the sixth embodiment will mainly be described below.

Referring to FIG. 15, compared with the blood-pressure measuring apparatus 1 of the first to fourth embodiments, a blood-pressure measuring apparatus 1 of the sixth embodiment further includes an eye mask 8 for measuring movement of the eye which is of the biological information on the subject. The eye mask 8 is attached to a head H of the subject.

Figure 16:
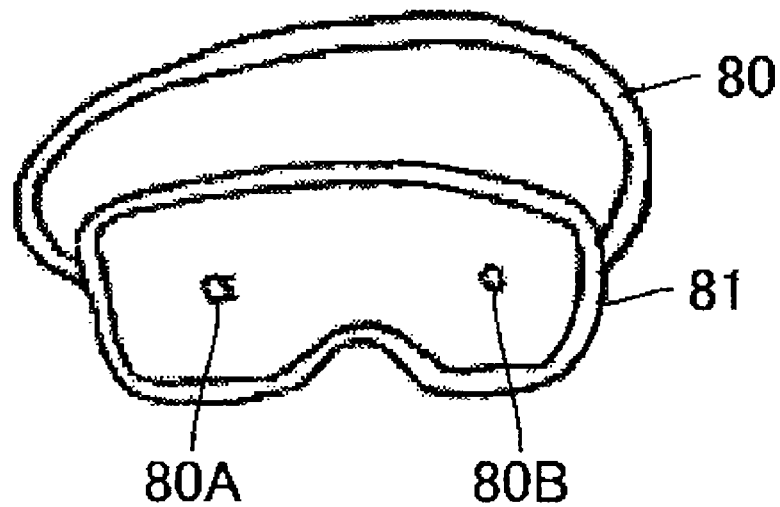
FIG. 16 is an enlarged view showing an eye mask of FIG. 15.

FIG. 16 is an enlarged view showing the eye mask 8. The eye mask 8 includes a belt 80 which fixes the eye mask 8 to the head H of the subject and a plate-like portion 81. A right-eye infrared sensor 80A and a left-eye infrared sensor 80B are provided in the plate-like portion 81. The right-eye infrared sensor 80A and the left-eye infrared sensor 80B are infrared sensors corresponding to the right eye and the left eye of the subject respectively. A converter 82 which converts outputs of the infrared sensors into the pieces of digital data is provided between the eye mask 8 and a main body of the blood-pressure measuring apparatus 1.

Figure 17:
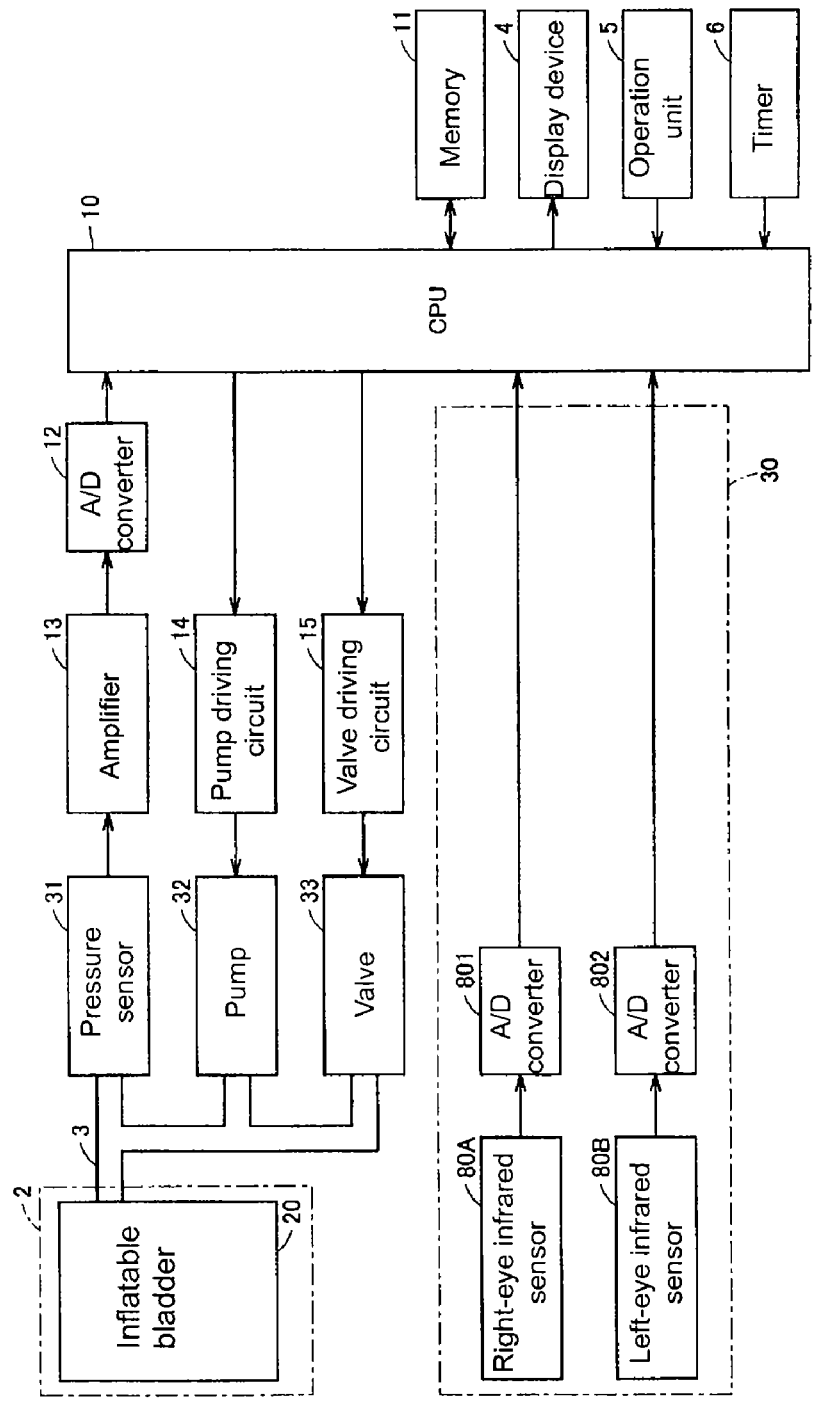
FIG. 17 is a schematic diagram showing a hardware configuration of the blood-pressure measuring apparatus 1 of FIG. 15.
Figure 18:
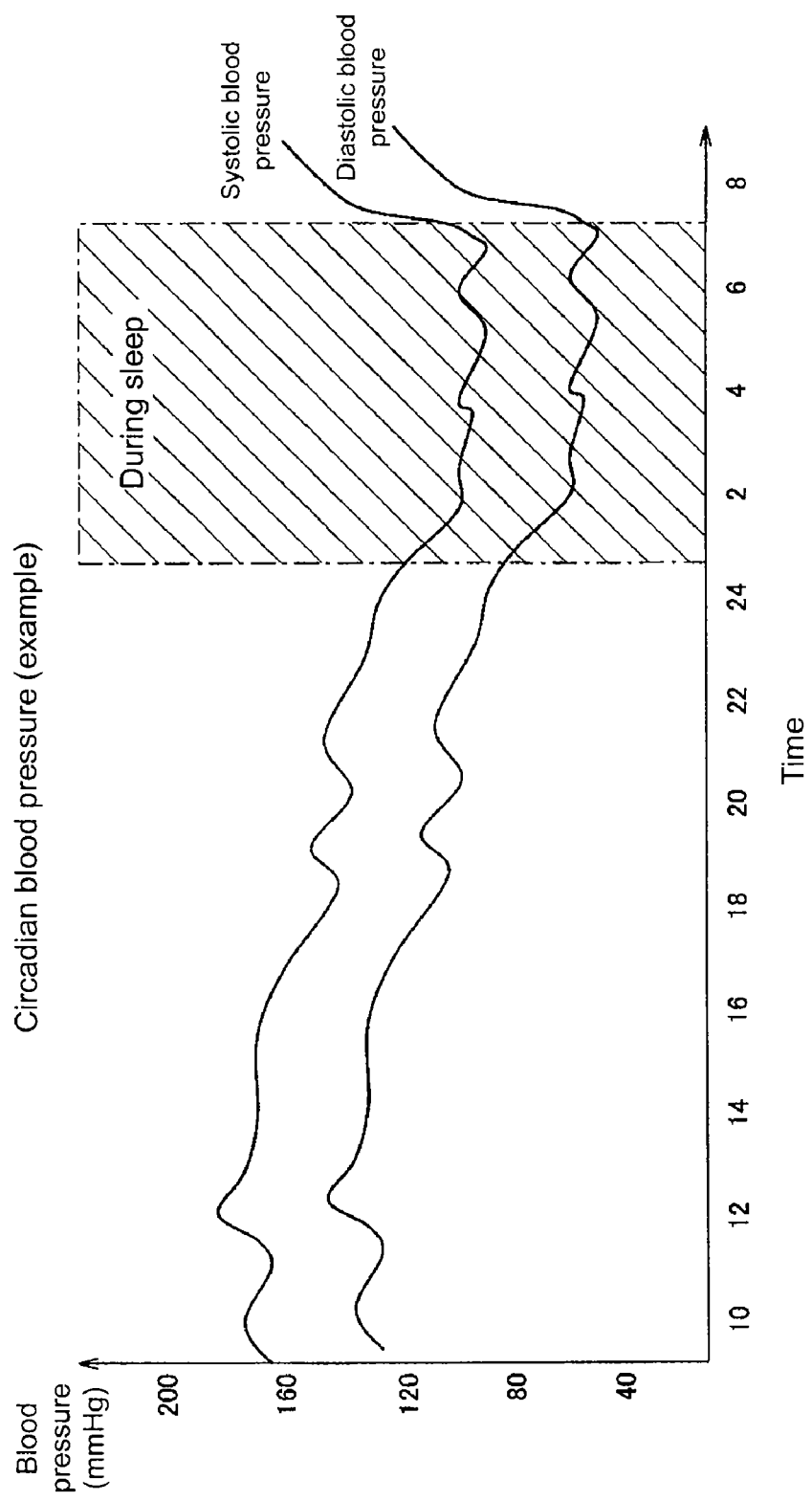
FIG. 18 is a diagram generally showing daily fluctuations in systolic blood pressure value and diastolic blood pressure value of a human.

FIG. 17 is a schematic diagram showing a hardware configuration of the blood-pressure measuring apparatus 1 of FIG. 15. Compared with the blood-pressure measuring apparatus 1 of the first to fourth embodiments, the blood-pressure measuring apparatus 1 of the sixth embodiment includes the right-eye infrared sensor 80A and left-eye infrared sensor 80B and A/D converters 801 and 802. The A/D converters 801 and 802 convert the outputs of the right-eye infrared sensor 80A and left-eye infrared sensor 80B into the pieces of digital data. The A/D converters 801 and 802 are included in the converter 82.

In the sixth embodiment, the right-eye infrared sensor 80A and left-eye infrared sensor 80B detect the movement modes of the eyes, and the sleep depth of the subject is determined based on the detected movement modes.

The sixth embodiment differs from the first to fourth embodiments only in that the biological information measured to determine the sleep depth is changed. That is, the control content in which the determined sleep depth is utilized is similar to those of the first to fourth embodiments.

Some methods of determining the sleep depth are described in the embodiments of the present invention. In the present invention, the sleep depth may be determined by other methods different from the above-described methods.

For other methods, examples of the biological information on the subject include a brain wave, an electrocardiogram, a muscle potential, the body motion, and a breathing cycle.

In the embodiments, the blood pressure value of the subject is measured when the sleep depth satisfies the predetermined condition. Alternatively, a switch is provided in the blood-pressure measuring apparatus 1, the switch is turned on immediately before the subject is asleep, and the blood-pressure measuring apparatus 1 may measure the blood pressure under the condition that a predetermined time (for example, one hour, one and a half hours, and two hours) elapsed since the switch is turned on. It is thought that the blood pressure can be measured by performing the blood pressure measurement in the above-described way, when the subject is daily in the sleep state.

The embodiments are described only by way of example, and it is to be understood that the present invention is not limited to the embodiments. The scope of the present invention is shown by not the embodiments but only claims, and it is intended that meanings equivalent to claims and all the modifications and changes within the scope of the present invention are included. Each of the embodiments is intended to be realized by a combination of the embodiments as much as possible.

According to the present invention, the level of sleep of the subject is determined, and the blood pressure value is stored when the determined level of sleep satisfies the predetermined condition. Therefore, the blood pressure value is stored as the measurement value when the sleep depth of the subject satisfies the predetermined condition. Accordingly, the blood pressure value can be measured based on the sleep depth of the subject during the non-REM (non-Rapid Eye Movement) sleep or the uprising suitable to the measurement of the blood pressure value.

The invention claimed is:

1. A blood-pressure measuring apparatus comprising:
a blood-pressure measuring unit which measures a blood pressure value of a subject;
a level determination unit which determines at constant time intervals a level of sleep of the subject from at least three levels except for awakening;
a storage unit in which information specifying a condition for the determined level of sleep is stored;
a judgment unit which judges whether or not the determined level of sleep satisfies the condition specified by the information stored in the storage unit, wherein the judgment unit judges that the condition is satisfied when the level of sleep determined by the level determination unit differs by more than a specific amount from a level of sleep previously determined by the level determination unit;
a blood-pressure measuring start unit which causes the blood-pressure measuring unit to start blood pressure measurement when the judgment unit judges that the determined level of sleep satisfies the condition; and
a blood pressure value storage unit in which the blood pressure value of the subject measured by the blood-pressure measuring unit is stored in response to an instruction from the blood-pressure measuring start unit.

2. The blood-pressure measuring apparatus according to claim 1, wherein the blood-pressure measuring apparatus is connected to a biological information measuring unit which measures biological information on the subject, and the level determination unit determines the level of sleep of the subject based on the measurement result of the biological information measuring unit.

3. The blood-pressure measuring apparatus according to claim 2, wherein the biological information measuring unit measures a pulse of the subject, and
the level determination unit determines the level of sleep of the subject based on a change in pulse wave period measured by the biological information measuring unit.

4. The blood-pressure measuring apparatus according to claim 2, wherein the biological information measuring unit measures a body temperature of the subject, and
the level determination unit determines the level of sleep of the subject based on a change in body temperature measured by the biological information measuring unit.

5. The blood-pressure measuring apparatus according to claim 1, 2, 3 or 4, wherein the judgment unit judges that the condition is satisfied when a depth of the determined level of sleep reaches the deepest level in levels which can be determined by the level determination unit.

6. The blood-pressure measuring apparatus according to claim 1, 2, 3 or 4, wherein the judgment unit judges that the condition is satisfied when a depth of the determined level of sleep is changed from a second shallowest level to a shallowest level of the sleep levels which can be determined by the level determination unit.

* * * * *

UNITED STATES PATENT AND TRADEMARK OFFICE
CERTIFICATE OF CORRECTION

| | | |
|---|---|---|
| PATENT NO. | : 8,251,913 B2 | |
| APPLICATION NO. | : 12/280967 | |
| DATED | : August 28, 2012 | |
| INVENTOR(S) | : Akihisa Takahashi et al. | |

It is certified that error appears in the above-identified patent and that said Letters Patent is hereby corrected as shown below:

On the Title page, under Section (73) Assignee:

Please add -- Jichi Medical University, Shimotsuke-shi (JP) --

Signed and Sealed this
First Day of January, 2013

David J. Kappos
*Director of the United States Patent and Trademark Office*